United States Patent [19]
Gurevich

[11] Patent Number: 6,124,352
[45] Date of Patent: Sep. 26, 2000

[54] ANTIFUNGAL AGENTS

[75] Inventor: Vladimir Z. Gurevich, Madison, Wis.

[73] Assignee: Jemlan, LLC, Madison, Wis.

[21] Appl. No.: 08/281,246

[22] Filed: Jul. 27, 1994

Related U.S. Application Data

[63] Continuation of application No. 08/012,671, Feb. 3, 1993, abandoned, which is a continuation-in-part of application No. 07/846,199, Mar. 4, 1992, abandoned.

[51] Int. Cl.$^7$ .......................... A61K 31/265; A61K 31/21
[52] U.S. Cl. .......................... 514/512; 514/513; 514/514; 514/858
[58] Field of Search .................................... 514/512, 513, 514/514, 858

[56] References Cited

U.S. PATENT DOCUMENTS

| | | | |
|---|---|---|---|
| 2,841,521 | 7/1958 | Abramitis | 514/70 |
| 2,841,522 | 7/1958 | Wolf | 514/535 |
| 4,404,216 | 9/1993 | Richardson | 514/383 |
| 4,767,777 | 8/1988 | Bass et al. | 514/383 |
| 4,806,151 | 2/1989 | Bohus et al. | 504/322 |

FOREIGN PATENT DOCUMENTS

| | | |
|---|---|---|
| 0 183 494 | 6/1985 | European Pat. Off. . |
| 53-101528 | 9/1978 | Japan . |
| 1160696 | 5/1982 | U.S.S.R. . |

OTHER PUBLICATIONS

Chemical Abstracts 89: 179658; Motrenko et al., 1978.
Boyle, et al., *Annals N.Y. Acad. Science*, vol. 544, pp. 86–100 (1988).
Georgopapadakou, et al., "Effect of Antifungal Agents on Lipid Biosynthesis and Membrane Integrity in *Candida albicans*," *Antimicrobial Agents and Chemotherapy*, vol. 31(1):46–51 (1987).
Hitchcock, et al., "The Lipid Composition and permeability to the Triazole Antifungal Antibiotic ICI 153066 of Serum–grown Mycelial Cultures of *Candida albicans*," *Journal of General Microbiology*, 135:1949–1955 (1989).
Lipschik, G. Y. and J. A. Kovacs, "chemotherapeutic Targets in *Pneumocystis carinii*," *Emerging Targets in Antibacterial and Antifungal Chemotherapy*, Sutcliffe, J. and N. H. Georgopapadakou, eds., pp. 568–588 (1992).
Motrenko, et al., translated from *Zh. Org. Khim*, vol. 14, pp. 1669–1676 (1978).
Richardson, et al., "Activity of UK–49,858, a Bis–Triazole Derivative, Against Experimental Infections with *Candida albicans* and *Trichophyton mentagrophytes*," *Antimicrobial Agents and Chemotherapy*, vol. 27(5):832–835 (1985).
Shepherd, et al., *J. Gen. Microbiol.*, vol. 93, pp. 361–370 (1976).
Shepherd, et al., *Can. J. Microbiol.* vol. 26, pp. 21–26 (1990).
Troke, et al., *Antimicrob. Agents & Chemotherapy*, vol. 28, pp. 815–818 (1985).
Van't Wout, et al., *Antimicrob. Agents & Chemotherapy*, vol. 33, pp. 147–151 (1989).
Vidotto, et al., *Mycopathologia*, vol. 100, pp. 7–15 (1987).

*Primary Examiner*—Kevin E. Weddington

[57] ABSTRACT

A method of treating fungal diseases as well as pharmaceutical, veterinary and agricultural compositions useful in such treatment. The method includes administering an effective antifungal amount of a compound of the formula (I):

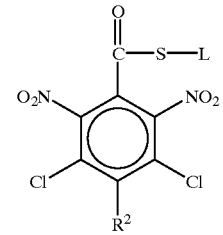

wherein S is a spacer selected from a nitrogen, an oxygen, an alkyl, an alkenyl, an alcohol, an ester, a polyester, an amino acid, a carbohydrate, or a nitrogen-containing positively charged group;

L is a ligand selected from a hydrogen, a hydroxyl residue, an alkyl residue, an alkenyl residue, a benzyl residue, an alcohol residue, an ester residue, a polyester residue, an alkyl acid residue, a carbohydrate, a steroid, a lipid, an organic polymer, a nitrogen-containing positively charged group or a vitamin;

$R_1$ and $R_3$ are halogen or hydroxyl; and $R_2$ is hydrogen or alkyl.

13 Claims, 1 Drawing Sheet

ANTIFUNGAL AGENTS

This is a continuation, of application Ser. No. 08/012,671 filed Feb. 3, 1993 now abandoned which is a continuation-in-part of application Ser. No. 07/846,119 filed Mar. 4, 1992, now abandoned.

FIELD OF THE INVENTION

This invention relates to biologically active, dinitrobenzoic acid compounds and derivatives thereof, and specifically to methods of treating fungal diseases using these compounds.

BACKGROUND OF THE INVENTION

For many years, the development of effective therapeutic agents for fungal diseases (mycoses) has lacked the attention devoted to drugs effective against other infective organisms. The most common mycotic infections are superficial in nature, are not life threatening, and provide little medical impetus to pharmaceutical companies to develop novel treatments. This scenario is changing, however, and while death from fungal disease is not new, the incidence of systemic fungal infections that cause these fatalities is increasing. Ironically, advances in modern medical techniques in other fields (immunosuppressive and/or cytotoxic therapy) and the advent of disease such as Acquired Immuno Deficiency Syndrome (AIDS) are major contributing causes to the increased number of serious fungal infections.

Fungal diseases can, thus, be divided into the life-threatening systemic infections, such as histoplasmosis, systemic candidiasis, aspergillosis, blastomycosis, coccidioidomycosis, paracoccidioidomycosis, and cryptococcosis, and the more common superficial ones, such as dermatophyte (ringworm) infections, for example, tinea pedis (athlete's foot) and tinea cruris (jock itch), candidiasis, and actinomycosis. The life-threatening fungal infections are a growing problem not only for immunosuppressed or immunocompromised individuals as noted above but individuals with other viral infections, such as cytomegalovirus (CMV), and influenza, for cancer patients receiving chemotherapy or radiotherapy, for transplant patients receiving antirejection agents, and for patients that have received toxic chemicals, metals and radiation exposure.

Mycoses are often caused by fungi which are opportunists, rather than pathogens. Candidiasis, aspergillosis, phycomycosis, nocardiosis, and cryptococcosis are typically opportunistic fungal infections. For example, *Candida albicans*, is normally found in the alimentary tract as a commensal, yet it is a major cause of systemic fungal infections in immunocomprised patients and topical infections in healthy individuals.

Most drugs currently available for the treatment of mycoses have limited efficacy or are poorly tolerated. A persistent and vexatious problem with antifungal agents, largely unattended by the prior art, is the lack of an agent that is easy and economical to synthesize, and possesses high activity and broad spectrum activity against organisms, low toxicity and limited adverse effects.

Moreover, many known agents merely have fungistatic properties, rather than fungicidal properties. Fungistatic activity is the ability to prevent growth of fungi, while fungicidal (fungitoxic) activity is the ability to kill the fungi. Many agents used in the treatment of superficial mycoses are virtually devoid of either fungistatic or fungicidal actions in the concentrations used, and their beneficial effects probably depend upon factors not related to any direct effect on fungi.

Among the known antifungal agents are the azoles such as imidazoles and triazoles, the polyene macrolide antibiotics, such as nystatin and amphotericin B. as well as the keratolytic agents. The imidazoles and triazoles include ketoconazole, fluconazole, itraconazole miconazole, clotrimazole, and econazole. See, for example, U.S. Pat. No. 4,767,777 issued to Bass et al.; U.S. Pat. No. 4,404,216 issued to Richardson; European Patent Application 0 183 494; F. T. Boyle et al., *Annals N. Y. Acad. Science*, vol. 544, pp. 86–100 (1988); P. F. Troke et al., *Antimicrob. Agents & Chemotherapy*, vol. 28, pp. 815–818 (1985) and vol. 27, pp. 832–835 (1985). These drugs have been used in both topical and oral preparations to treat both superficial and systemic infections. The most notable is ketoconazole. However, toxicity (e.g., nausea, anorexia, vomiting) prevents its use in oral form and these together with problems of teratogenicity, enzyme specificity, as well as an idiosyncratic hepatotoxicity syndrome have severely curtailed the usage of this compound.

Amphotericin B and nystatin are most notable among the polyene macrolide antibiotics. Topically, these agents are effective against candidiasis of the skin and mucous membrane, but not against ringworm. Amphotericin B is most effective against systemic fungal infections. However, this drug is not soluble in water and must be prepared in colloidal preparations for intravenous or intrathecal(into the cerebral spinal fluid) use. Sodium or potassium salts must be added to prevent precipitation of the colloid. This drug also cannot be given intramuscularly or orally. Amphotericin B has many adverse effects including severe febrile reaction which almost always occurs. Renal toxicity, hypokalemia, anemia, nausea, weight loss, and phlebitis are also common side effects. For a comparison of efficacies of amphotericin B with fluconazole and itraconazole, see Van't Wout et al., *Antimicrob. Agents & Chemotherapy*, vol. 33, pp. 147–151 (1989).

The keratolytic agents such as salicylic acid and benzoic acid exert their effect mainly by promoting desquamation of the stratum corneum, especially in hyperkeratotic locations. The fungus resides in the stratum corneum, where keratin is its substrate, not in the toxininduced lesion. Thus, keratosis removes the offending fungus as well as aids in the penetration of drugs.

Other topical agents include undecylenic acid, ciclopirox olamine, haloprogin, and tolnaftate. Undecylenic acid (10-undecenoic acid) is one of several fatty acids and their salts which exhibit primarily fungistatic activity. Ciclopirox olamine and haloprogin have a spectrum of activity similar to the imidazoles. Tolnaftate is very effective against ringworm infections but not effective against Candida species.

In addition to the keratolytic action of benzoic acid, in the agricultural field, certain substituted benzoic acid compounds, that is, certain monosubstituted dinitrobenzoic acid compounds, have been reported to have fungicidal properties. For example, 4-chloro-3,5-dinitrobenzoic acid ester is a known fungicide (see, e.g., Japanese Patent Application 53101528) although reported to be phytotoxic to certain cultivated plants. See U.S. Pat. No, 4,806,151 issued to Bohus et al. U.S. Pat. No. 4,806,151 discloses 4-amino-3,5-dinitrobenzoic compounds having fungicidal as well as herbicidal properties, and suggests that such compounds are not phytotoxic to cultivated plants. While these monosubstituted dinitrobenzoic acid compounds are typically potent fungicides, their toxicity is far too great for animal or human use.

It is noted, however, that the use of 3,5-dichloro-2,6-dinitrobenzoic acid as an antituberculant agent has been disclosed in Russian Patent 1160696 issued to O. F. Ginsburg, V. Z. Gurevich et al.

Thus, despite the plethora of agents which have or are alleged to have antifungal properties, most are simply fungistatic and not fungitoxic. For those that are fungicidal, for example, amphotericin B, there are severe dverse side effects which limit their use and their hemical properties, e.g., solubility, limit drug delivery method. Although opportunistic systemic fungal infections have a high morbidity and mortality and their incidence is increasing, the art has yet to provide a safe, effective water soluble, simple-to-synthesize, fungitoxic agent with a broad antifungal spectrum of activity coupled with limited adverse effects and low toxicity.

SUMMARY OF THE INVENTION

The present invention provides safe, effective, shelf-stable, water soluble, simple-to-synthesize, fungitoxic compounds with a broad antifungal spectrum of activity coupled with limited adverse effects and low toxicity. The compounds of the invention include dinitrobenzoic acids and derivatives thereof, and the invention provides methods of treating fungal infections using these compounds.

In one aspect, the invention is a pharmaceutical composition useful for treating fungal infections. The composition consists of a compound of formula (I) as defined hereinbelow and addition salts, hydrates and solvates thereof in combination with a pharmaceutically acceptable vehicle. The amount of the compound of formula (I) is an effective antifungal amount and is preferably in a unit dose about 1.0 mg to about 4000 mg. The preferred compounds of formula (I) are 3,5-dihalo-2,6-dinitrobenzoic acids and their derivatives.

One form of the pharmaceutical composition is a sustained release formulation of the compound of formula (I) in a lipid-soluble form.

In another embodiment, the invention provides a method for treating fungal infections and diseases which includes administering an effective antifungal amount of a compound of formula (I). The compound of formula (I) is preferably administered orally, intramuscularly, intravenously or topically. The daily dose of the compound of formula (I) is about 1 mg to about 100 mg per kg of body weight of the treated patient.

Other advantages and a fuller appreciation of the specific adaptations, compositional variations, and physical and chemical attributes of the present invention will be gained upon an examination of the following detailed description of the invention, taken in conjunction with the accompanying drawings.

BRIEF DESCRIPTION OF THE DRAWINGS

The present invention will hereinafter be described in conjunction with the appended drawings, wherein like designations refer to like elements throughout and in which.

DETAILED DESCRIPTION

Figure 1:
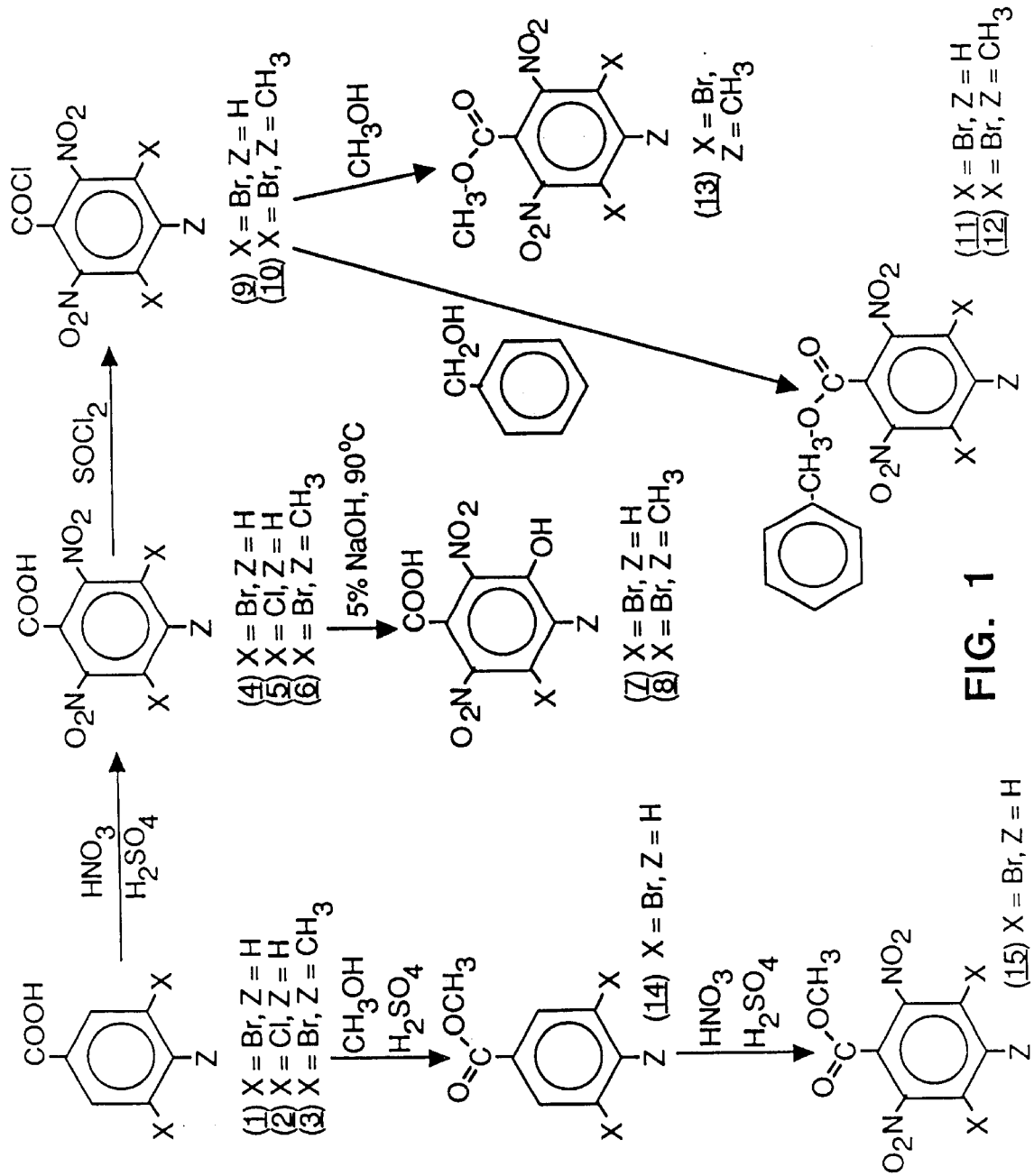
FIG. 1 illustrates preparative steps for the synthesis of various dinitrobenzoic compounds and derivatives.

The present invention provides a method of treating fungal diseases as well as pharmaceutical, veterinary and agricultural compositions useful in such treatment. The method utilizes and the compositions contain as active ingredients certain dinitrobenzoic acid compounds and derivatives. These compounds and derivatives are characterized by certain advantageous attributes: water solubility, low molecular weight, economical production, shelf-stability, and low toxicity.

As used herein, the terms "biological activity" or "biologically active" are meant to refer to biochemical properties of compounds such as fungistatic or fungicidal properties. As used herein and generally in the art, the term "pharmaceutically acceptable addition salts" refers to those salts formed with strong bases which form nontoxic addition salts. Such salts may be obtained by conventional procedures, e.g., mixing solutions containing approximately equimolar amounts of the free acid and desired base, and the required salt is collected.

In one of its aspects, the invention encompasses methods of use of the biologically active compounds of the general formula (I):

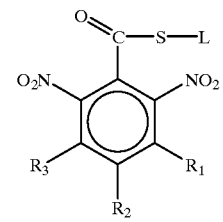

wherein S is a spacer selected from a nitrogen, an oxygen, an alkyl, an alkenyl, an amino acid, an alcohol, an ester, a polyester, a carbohydrate, or a positively charged group; L is a ligand selected from an hydroxy, an alkyl, an alkenyl, a benzyl, an alcohol, an ester, a polyester, an acid, a carbohydrate, a steroid, a lipid, a polymer, a positively charged group, or a vitamin; $R_1$ and $R_3$ are halogen or hydroxyl; and $R_2$ is hydrogen or alkyl. Preferred compounds among those of formula (I) are those in which $R_1$ and $R_3$ are both halogen, and $R_2$ is hydrogen or alkyl. It is noted that the compounds of formula (I) are disubstituted dinitrobenzoic acid derivatives and differ structurally, chemically and physiologically from previously reported monosubstituted dinitrobenzoic acid compounds which have fungicidal properties but have very high animal toxicity.

The compounds of formula (I) have been found to possess valuable antifungal activity, acting as fungicidal, not fungistatic, agents. The compounds of formula (I) are water soluble, permitting ease of use in systemic infections by all means of drug delivery systems. The compounds are simple and easy to make, using generally, as described hereinbelow, single step syntheses which do not involve any explosive solvents or expensive reagents. The low molecular weight of compounds of formula (I) provides a high probability of penetrating all tissues, including the blood-brain barrier into the cerebrospinal fluid.

It has also been found that the compounds of formula (I) have low toxicity, which enhances their pharmaceutical properties. Compounds of formula (I) have a toxicity, as measured by the $LD_{50}$ test, (e.g., $LD_{50}$ for 2,4-dibromo-3,5-dinitrobenzoic acid is 240 mg/kg) which is about sixty-fold lower than that for amphotericin B (i.e., $LD_{50}$ is 4 mg/kg). Thus, the compounds of the invention are applicable to various clinical and agricultural fields, and are particularly useful for the treatment of superficial and deep mycosis.

The compounds of formula (I) are prepared using syntheses similar to those described in Motrenko et al., translated from Zh. Org. Khim. vol. 14, pp. 1669–1676 (1978). For example, the compounds of formula (I) in which $R_1$ and $R_3$, both designated in FIG. 1 as X, are halogen, e.g., bromine or chlorine, and R$_2$, designated in FIG. 1 as Z, is hydrogen or methyl, are prepared according to the schema illustrated in FIG. 1. Specifically, the 3,5-dihalo-2,6-dinitrobenzoic acid or 4-methyl-3,5-dihalo-2,6-dinitrobenzoic acid, is prepared by nitration in the presence of sulfuric acid of the 3,5-dihalobenzoic acid or 4-methyl-3,5-dihalobenzoic acid. The methyl (or ethyl) esters are prepared by esterification with the appropriate alcohol of the 3,5-dihalo starting material in the presence of sulfuric acid, followed by nitration with nitric acid in the presence of sulfuric acid. To obtain the benzyl ester, the appropriate 3,5-dihalo-2,6-dinitro compound is reacted with thionyl chloride to form the chloroanhydride and then esterified with benzyl alcohol. The 3-hydroxy-5-halo-2,6-dinitro compounds can be formed by alkaline hydrolysis of the appropriate 3,5-dihalo-2,6-dinitro compound.

As detailed in the following examples, various ligands may be attached, by means of a spacer, to the compounds of formula (I), especially to the preferred 3,5-dihalo-2,6-dinitrobenzoic acid compounds. Appropriate ligands may be chosen which, for example, make the fungicidal compounds of the present invention more pharmacologically active or easier to deliver. The spacer may be a small group, such as an amino residue, or a larger residue which can bond to both the dinitrobenzoic acid derivative and to the ligand. While one may characterize a particular molecule attached to the acid residue of a compound of formula (I) as a spacer and ligand combination, it is often true that an attached molecule that includes a reactive group may equally correctly be considered as merely a spacer to which a separate ligand may subsequently be attached. For example, in the product of Example 13, the 6-aminohexanoic acid residue attached to C$_1$ may be characterized as a six carbon acid ligand bound to a nitrogen spacer. Alternatively, however, the 6-aminohexanoic acid may be equally well characterized merely as a spacer, in that it has at its terminus a reactive COOH group. Similarly, in Example 16, the allylamine residue of the product may be viewed as a spacer-ligand combination, or simply as a spacer. When the allylamine residue is viewed as a spacer-ligand combination, the product is a lipid soluble agent having antifungal activity at both the allylamine- and the aromatic portions of the molecule. When viewed as a spacer alone, the terminal double bond of the allylamine residue is a ready acceptor of a ligand.

In a further aspect, the invention entails a method of controlling fungal infections, such as for treating topical fungal infections caused by, e.g., Candida, and dermatophytes such as Trichophyton, Microsporum or Epidermophyton, or in mucosal infections caused by *Candida albicans* (e.g., oral thrush and vaginal candidiasis). The compounds of formula (I) are also useful for treatment of systemic fungal infections caused by, for example, *Candida albicans, Cryptococcus neoformans, Aspergillus flavus, Aspergillus fumigatus*, Coccidioides, Paracoccidioides, Histoplasma or Blastomyces. The compounds of formula (I) are particularly useful for treating fungal infections in immunocompromised patients such as patients with viral infections such as AIDS, CMV, and influenza, cancer patients receiving chemotherapy or radiotherapy, transplant patients receiving antirejection agents, and patients that have received toxic chemicals, metals and radiation exposure. The compounds of formula (I) are also effective against Hansen's disease (leprosy) which is caused by mycobacterium leprae or Hansen's bacillus.

The compounds of formula (I) are useful as active compounds in pharmaceutical compositions having reduced side effects and low toxicity as compared with the known antifungal agents, when used, for example, for systemic fungal diseases. Such compositions may include physiologically acceptable vehicles or carriers. These pharmaceutical compositions constitute another aspect of the invention.

The inventors evaluated the in vitro antifungal activity of the compounds by determining the minimum inhibitory concentration (M.I.C.), which is the concentration of the test compounds, in a suitable medium, at which growth of the particular microorganism fails to occur. The M.I.C. for *Candida albicans* was found to be 1.5 µg/ml. *Aspergillus fumigatus* and *Trichophyton* spp were also tested with similar results. Other microorganisms that may be used in such tests can include *Microsporum* spp, *Epidermophyton floccosum*, *Coccidioides immitis* and *Torulopsis glabrata*.

The relative in vitro efficacy of selected compounds of formula (I) are given in Table 1. These relative efficacy numbers were obtained by plating 100–150 cells of *Candida albicans* on replicate agar plates containing 15 µg of the named compound and by determining the relative growth inhibition of each compound.

TABLE 1

| Compound | Relative In Vitro Efficacy |
| --- | --- |
| 3,5-dibromo-2,6-dinitro benzoic acid | 100 |
| 3,5-dichloro-2,6-dinitro benzoic acid | 100 |
| 2,4-dicholoro-3,5-dinitro benzoic acid | 10 |
| methyl 3,5-dibromo-2,6-dinitro benzoate | 4 |

Additional in vitro evaluation of the antifungal activity of the compounds was performed by two independent testing laboratories. One laboratory found the minimum inhibitory concentration (µg/ml), in fungal strains, of 3,5-dichloro-2,6-dinitrobenzoic acid to range from 1.56 to 6.3 when nine fungal strains (*Candida* spp., *Cryptococcus neoformans, Aspergillus fumigatus*) were tested in HR/Mops broth and Sabouraud dextrose broth.

The second laboratory compared the minimum inhibitory concentrations (µg/ml) of 3,5-dichloro-2,6-dinitrobenzoic acid and Amphotericin B, an antifungal agent. The strains were plated, in the standard agar dilution method, on Isosensitest agar containing a single antifungal agent. Testing demonstrated broad specificity of the 3,5-dichloro-2,6-dinitrobenzoic acid against a wide range of fungi, but not against bacteria, with M.I.C. in the range of 4–31 µg/ml. While the compound demonstrated less fungal inhibition than Amphotericin B, it is important to note that the agar-plate test conditions were optimized to demonstrate Amphotericin B activity. Amphotericin B is water insoluble, while the test compound is water soluble. As such, when Amphotericin B is tested in agar, its activity appears higher than it would in vivo. In contrast, the water soluble test compound should demonstrate higher activity in vivo, since it would be free to migrate to an infection site.

Furthermore, the independent testing laboratory demonstrated the compound remained stable and active against *C. albicans* C316 in various broth media, even in the presence of 50% mouse serum, suggesting in vivo utility. Moreover, the compound was active (IC$_{50}$=17 µg/ml) against *Pneumocystis carinii* fungus removed from rat lungs and incubated in short term culture, where fungal viability was measured by incorporation of $^3$[H] para-aminobenzoic acid. In comparison, the IC$_{50}$ of pentamidine, the agent now widely used to counter *P. carinii* fungus infections, was 2 µg/ml.

The in vivo evaluation of the compounds can be carried out at a series of dose levels by intraperitoneal or intravenous injection or by oral administration, to mice which are inoculated with, e.g., a strain of *Candida albicans* or *Aspergillus flavus*. Activity is based on the survival of a treated group of mice after the death of an untreated group of mice. The dose level at which the compound provides 50 percent protection against the lethal effect of the infection ($PD_{50}$) is noted.

The pharmacologically active compounds of this invention can be processed in accordance with conventional methods of pharmacy to produce medicinal agents for administration to patients, e.g., mammals including human beings. For example, the compounds of formula (I) can be employed in admixtures with conventional excipients, e.g., pharmaceutically acceptable carrier substances suitable for enteral (e.g., oral), parenteral, or topical application which do not deleteriously react with the active compounds.

Suitable pharmaceutically acceptable carriers include but are not limited to water, salt solutions, alcohols, gum arabic, vegetable oils (e.g., corn oil, cottonseed oil, peanut oil, olive oil, coconut oil), fish liver oils, oily esters such as Polysorbate 80, polyethylene glycols, gelatine, carbohydrates (e.g., lactose, amylose or starch), magnesium stearate, talc, silicic acid, viscous paraffin, fatty acid monoglycerides and diglycerides, pentaerythritol fatty acid esters, hydroxy methylcellulose, polyvinyl pyrrolidone, etc.

The pharmaceutical preparations can be sterilized and, if desired, be mixed with auxiliary agents, e.g., lubricants, preservatives, stabilizers, wetting agents, emulsifiers, salts for influencing osmotic pressure, buffers, coloring, flavoring and/or one or more other active compounds, for example, other antifungal agents, vitamins, etc.

For parenteral application, particularly suitable are injectable, sterile solutions, preferably aqueous solution, which may contain other substances, for example, sufficient salts or glucose to make the solutions isotonic with the blood. They may also be administered as suspensions, emulsions, or implants, including suppositories. Ampoules are convenient unit dosages.

For enteral application, particularly suitable are tablets, dragees, liquids, drops, suppositories, lozenges, powders, or capsules. A syrup, elixir, or the like can be used if a sweetened vehicle is desired.

Sustained or directed release compositions can also be formulated, e.g., liposomes or those in which the active compound is protected with differentially degradable coatings, e.g., by microencapsulation, multiple coatings, etc. Particularly, in lipid-soluble form, the active compound can be released slowly and penetrate tissues and cell membranes.

Por topical application, suitable nonsprayable viscous, semi-solid or solid forms can be employed which include a carrier compatible with topical application and having a dynamic viscosity preferably greater than water. Suitable formulations include, but are not limited to, solutions, suspensions, emulsions, creams, ointments, powders, liniments, salves, aerosols, transdermal patches, etc., which are, if desired, sterilized or mixed with auxiliary agents, e.g., preservatives, stabilizers, emulsifiers, wetting agents, etc. Also suitable for topical application, are sprayable aerosol preparations wherein the active ingredient, preferably in combination with a solid or liquid inert carrier material, is packaged in a squeeze bottle or in admixture with a pressurized volatile, normally gaseous propellant.

For rectal administration, compounds are formed into a pharmaceutical composition containing a suppository base such as cacao oil or other triglycerides. To prolong storage life, the composition advantageously includes an antioxidant such as ascorbic acid, butylated hydroxyanisole or hydroquinone.

Oral, topical and intravenous administration of the pharmaceutical compositions of the present invention are preferred. Generally, the compounds of this invention are dispensed by unit dosage form comprising about 1 mg to about 4 g in a pharmaceutically acceptable carrier. The daily dosage of the compounds according to this invention generally is about 1 to about 100 mg/kg, preferably about 10 to about 100 mg/kg orally and about 1 to about 50 mg/kg intravenously.

It will be appreciated that the actual preferred amounts of active compound in a specific case will vary according to the efficacy of the specific compound employed, the particular compositions formulated, the mode of application, and the particular situs and organism being treated. For example, the specific dose for a particular patient depends on the age, body weight, general state of health, sex, on the diet, on the timing and mode of administration, on the rate of excretion, and on medicaments used in combination and the severity of the particular disorder to which the therapy is applied. Dosages for a given host can be determined using conventional considerations, e.g., by customary comparison of the differential activities of the subject compounds and of a known agent, such as by means of an appropriate conventional pharmacological protocol.

In yet another aspect, the compounds of the inventions can be used advantageous in veterinary compositions to treat fungal diseases such aspergillosis, candidosis, chromomycosis, coccidioidiocycosis, cryptococcosis, entomophthoromycosis, epizootic lymphangitis, geotrichosis, histoplasmosis, mucormycosis, mycetoma, north american blastomycosis, oomycosis, paecilimycosis, penicilliosis, rhinosporidiosis, and sprotrichiosis in animals. Generally, the compounds of this invention can be dispensed in unit dosage form comprising 2 mg to about 8 g in a suitable carrier. Preferably, the compounds of the inventions can be included in feed for the livestock, such that normal consumption of said feed provides about 1 mg to about 200 mg of at least one of the compounds of the invention per kg of animal per day. For large animals such as cows or horses, the daily dosage is suitably about 10 to about 40 g.

In a still further aspect, the compounds of the present invention can also be advantageously used in agricultural compositions, for example, compositions for plants and seeds to treat or prevent a variety of plant pathogenic fungi, including rusts, mildews, and molds. Generally, the compounds of the present invention are dispensed in the form of dusting powders, granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture, and they are manufactured in accordance with conventional procedures. The compositions typically contain from 0.01 to 10 wt %, preferably 0.1 to 1 wt. % of the active ingredient. The compositions may also incorporate other active ingredients, for example, compounds having herbicidal or insecticidal activity or a further fungicide. The compounds and compositions can be applied in a number of ways, for example, they can be applied directly to the plant foliage, stems, branches, seeds or roots or to the soil or other growing medium and they may be used not only to eradicate disease, but also prophylactically to protect the plants or seeds from attack. For field use, likely application rates of active ingredient are about 100 to 10,000 g/acre.

The following examples are to be construed as merely illustrative, and not limitative of the remainder of the disclosure in any way whatsoever. In the following examples, all temperatures are set forth in degrees Celsius. The purities of the compounds were checked by thin-layer chromatography (TLC) on Silufol UV-254 plates or Silica Gel 60 F-254 plates.

The following systems were used as eluents in TLC: (1) chloroform; (2) 20:20:1 mixture of chloroform, diethyl ether and acetic acid; (3) 5:2 mixture of 2-butanol and 3% ammonia; (4) 1:1 mixture of chloroform and petroleum ether (5) 50:25:25 mixture of heptane, methanol and ethyl acetate; (6) 95:4:1 mixture of chloroform, methanol, and acetic acid; (7) 50:40:10 mixture of heptane, chloroform and methanol; and (8) methanol.

$R_f^n$ is the $R_f$ value for the particular TLC eluent system used, e.g., $R_f^2$ is the $R_f$ value for system 2 eluent described above.

EXAMPLE 1

Synthesis of 3,5-dibromo-2,6-dinitrobenzoic acid

To 150 ml of nitric acid (density=1.50) is gradually added with stirring 150 g of 3,5-dibromobenzoic acid (1 in FIG. 1) and then 400 ml of sulfuric acid (density=1.83) so that the temperature of the mixture does not rise above 60° C. The mixture is then carefully heated to 90–100° C. and stirred at this temperature of 6–10 hr. The treatment is stopped when the mononitro compound ($R_f^2$=0.66) has disappeared from the reaction mixture. At the end of the nitration, the reaction mixture is cooled, and the precipitate is filtered off, washed with sulfuric acid (density=1.83), mixed with 150 g of crushed ice, refiltered, and washed with water to the absence of sulfate ion in the water. 184 g (96%) of the dibromodinitro compound (4) is obtained. It is chromatographically homogeneous in system 2; m.p. 214–215° C. PMR spectrum (in acetone), δ, ppm: 8.44(s, 1H, ArH$^4$). %N is found to be 7.86, 8.21; $C_7H_2N_2Br_2O_6$; calculated %N=7.57.

EXAMPLE 2

Synthesis of 3,5-dichloro-2,6-dinitrobenzoic acid

To 150 ml of nitric acid (density=1.50) is gradually added with stirring 102.3 g of 3,5-dichlorobenzoic acid (2) and then 400 ml of sulfuric acid (density=1.83) so that the temperature of the mixture does not rise above 60° C. The mixture is then carefully heated to 77° C. and stirred at this temperature for 6–10 hr. The treatment is stopped when the mononitro compound ($R_f^2$=0.66) has disappeared from the reaction mixture. At the end of the nitration, the reaction mixture is cooled, and the precipitate is filtered off, washed with sulfuric acid (density=1.83), mixed with 150 g of crushed ice, refiltered, and washed with water to the absence of sulfate ion in the water. A 144.5 g (96%) of the dichlorodinitro compound (5) is obtained. It is chromatographically homogeneous in system 2; m.p. 205° C. PMR spectrum (in acetone), δ, ppm: 8.44 (s, 1H, ArH$^4$). %N is found to be 9.64, 10.15%; $C_7H_2C_{12}N_2O_6$; calculated %N=9.96.

EXAMPLE 3

Synthesis of benzyl 3,5-dibromo-2,6-dinitrobenzoate

A mixture of 3.6 g of 3,5-dibromo-2,6-dinitrobenzoic acid (4) and 20 ml of thionyl chloride is boiled for 3 hr. The excess of thionyl chloride is distilled under vacuum. To the obtained chloride (9) of compound, 10 ml of benzyl alcohol is added and the mixture is stirred at 40° C. for 3–4 hr. The benzyl alcohol is then distilled under vacuum ($p_{res}$=2–4 mm Hg), and the residue is dissolved in 30 ml of chloroform. The solution is washed with water and 1% sodium bicarbonate solution, and dried with calcium chloride. The chloroform is distilled under vacuum, and the residue is crystallized from benzene. A 1.6-g yield (37%) of the benzyl ester (11) is obtained; mp 190–192° C.

PMR spectrum (in acetone), δ, ppm: 8.64 (s, 1H, ArH$^4$), 7.44 (s, 5H, Ph), 5.40 (s, 2H, COOCH$_2$Ph). Found %: Br 35.46, 35.57; N 6.17, 6.46. $Cl_4H_8Br_2N_2O_6$; calculated %: Br 34.73; N 6.08.

EXAMPLE 4

Synthesis of methyl 3,5-dibromo-2,6-dinitrobenzoate

An 8.5-g sample of 3,5-dibromobenzoic acid (1) in a mixture of 80 ml of methanol and 10 ml of sulfuric acid (d=1.83) is boiled for 5–6 hr. After cooling, the precipitate is filtered off. The filtrate is evaporated to half under vacuum, the residue is diluted with water, and the precipitate is filtered off. It is added to the previous portion and stirred with 50 ml of water. A 10% solution of sodium bicarbonate is added to the obtained mixture to pH 7.5. The ester is filtered off, washed with water, and dried in air, and then over calcium chloride in a vacuum desiccator. A 7.9-g yield (89%) of compound (14) was obtained. The product was chromatographically homogeneous in system 1; mp 62–63° C.

To 84 ml of nitric acid (density=1.50), while stirring, is added 22 g of methyl 3,5-dibromobenzoate (14) and, then, gradually 160 ml of sulfuric acid (density=1.83). Here the temperature of the reaction mixture must not be higher than 40° C. When the sulfuric acid had been added, the reaction mixture is slowly heated to 90–100° C. and kept at this temperature for 15–20 h. The end of nitration is judged from the disappearance of the mononitro compound ($R_f^1$=0.53) from the reaction mixture. After cooling the precipitate is filtered off, washed with sulfuric acid (density=1.83), mixed with ice water, filtered, and washed with water to the absence of sulfate ion in the water. A 27.9-g yield (97%) of compound (15) chromatographically homogeneous in system 2 is obtained; mp 168–170° C. (from carbon tetrachloride).

EXAMPLE 5

Synthesis of 3-bromo-2,6-dinitro-5-hydroxybenzoic acid

A solution of 60 g of 3,5-dibromo-2,6-dinitrobenzoic acid (4) in 600 ml of 95% sodium hydroxide is heated at 45–50° C. for 30 h. The end of the reaction is judged from the disappearance of the initial compound ($R_f^3$=0.35). The reaction mixture is then evaporated under vacuum ($p_{res}$=20–30 mm Hg) to a volume of 150–200 ml, and 120 ml of hydrochloric acid (density=1.19) is added with stirring and cooling. The acid is separated as an oil, which soon begins to crystallize. The precipitate is filtered off, washed with 10% hydrochloric acid and with petroleum ether, and dried. A 45-g yield (90%) of compound (7) wherein X=Br is obtained; mp 174–175° C. (from benzene). Found %: Br 26.77, 26.40; N 9.19, 9.41. $C_7H_3BrN_2O_6$; calculated %: Br 26.02; N 9.12.

EXAMPLE 6

Synthesis of 3,5-dibromo-2,6-dinitro-4-methylbenzoic acid

To 50 ml of nitric acid (density=1.50), while stirring, is gradually added 34 g of 3,6-dibromo-4-toluic acid (3) and then 148 ml of sulfuric acid (density=1.83) so that the temperature does not rise above 40° C. The reaction mixture is gradually heated to 80–90° C. and kept at this temperature for 7–8 hr. The end of the reaction is judged from the disappearance of the mononitro compound ($R_f^2$=0.53). After cooling, the precipitate is filtered off, washed with sulfuric acid (density=1.83), mixed with iced water, refiltered, washed with water to the absence of sulfate ion in the water, and dried. A 36-g yield (80%) of compound (6) is obtained; decomposition pt. 229–231° C., (from 70% alcohol). Found %: Br 40.26, 40.28; N 6.98, 7.19. $C_8H_4Br_2N_2O_6$; calculated %: Br 41.66; N 7.29.

EXAMPLE 7
Synthesis of methyl 3,5-dibromo-2,6-dinitrotoluate

A mixture of 3 g of 3,5-dibromo-2,6-dinitro-4-toluate (6) and 15 ml of thionyl chloride is boiled for 3 h until the initial product is completely dissolved. The excess of thionyl chloride is distilled under vacuum, 30 ml of methanol is added to the residue, and the mixture is boiled for 2 h. After cooling, the precipitate is filtered off and washed with ether. A 2.4-g yield (77%) of the methyl ester (13) chromatographically homogeneous in system 1 was obtained; mp 199–201° C. (from methanol).

EXAMPLE 8
Synthesis of benzyl 3,5-dibromo-2,6-dinitro-4-methylbenzoate

A mixture of 20 g of 3,5-dibromo-2,6-dinitro-4-methylbenzoic acid (6) and 70 ml of thionyl chloride is boiled for 5–8 h until the initial compound is completely dissolved. The excess of thionyl chloride is distilled under vacuum, 60 ml of benzyl alcohol is added to the residue, and the mixture is heated at 40° C. for 2–3 h. After cooling, the precipitate is filtered off and washed with petroleum ether. A 17-g yield (69%) of the benzyl ester (12) chromatographically homogeneous in system 4 is obtained; mp 147–150° C. (from benzene). Found %: Br 34.27, 34.10; N 6.00, 6.09. $C_{15}H_{10}Br_2N_2O_6$; calculated %: Br 33.71; N 5.90.

EXAMPLE 9
In Vitro fungicidal test

The antifungal activities of the compounds of formula (I), amphotericin B and ketoconazole were tested.

The 10% w/w malt extract, 2% agar solution used for plating in this test was prepared by mixing 100 g malt extract, 20 g agar, and a pellet of sodium hydroxide (about 0.1 g) in 1 liter of distilled, deionized water (DDW). This solution was sterilized by autoclaving, and then poured into plates. See, Kreger-van Rij, *The Yeast: A Taxonomic Study*, Elsevier, Amsterdam, p. 1082.

The yeast-malt (YM) broth was composed of 3 g yeast extract, 3 g malt extract, 5 g peptone, and 10 g glucose in 1 liter DDW. The solution was brought to pH 7.2 with inorganics (e.g., hydrochloric acid or sodium hydroxide), then sterilized by autoclaving.

Stock solutions of the drugs to be tested were made in a mixture of dimethylformamide (DMF) and 0.05 M phosphate buffer at pH 7.2, combined in a 4:6 ratio of DME to buffer. Test solutions of 1 mg/ml solutions were prepared.

Two control solutions were prepared. One was the phosphate buffer as described above, the other was a mixture of DMF and the buffer in a 4:6 ratio as described above.

All drug and control solutions were sterilized by filtration through a 0.2 g filter.

3.6 ml of a suspension of *Candida albicans* ($A_{600}$= 0.11–0.19) was mixed with 0.4 ml of each of 3,5-dichloro-2,6-dinitro benzoic acid, amphotericin B and ketoconazole (1 mg/ml) (final concentration 0.1 mg/ml) and was shaken at 200 rpm at 30° C. for 80 min. (For growth characteristics of *Candida albicans*, see, for example, M. G. Shepherd et al., *J. Gen. Microbiol.*, vol. 93, pp. 361–370 (1976); M. G. Shephard et al., *Can. J. Microbiol.*, vol. 26, pp. 21–26 (1980); Vidotto et al., *Mycopatholocia*, vol. 100, pp. 7–15 (1987)) A series of agar plates, was inoculated with the above admixture, plating 150 μl/plate diluted a thousand-fold with YM broth, and each plate was then incubated for 48 hours at 30° C. The number of colonies were counted for each plate as shown in Table 2.

TABLE 2

| Plate No. Group | Fungicidal Test as Number of Colonies/Plate | | | | | | | | |
|---|---|---|---|---|---|---|---|---|---|
| | 1 | 2 | 3 | 4 | 5 | 6 | 7 | 8 | 9 |
| Control | 93 | 63 | 56 | 102 | 109 | 110 | 115 | 118 | 111 |
| 3,5-dichloro-2,6-dinitro-benzoic acid | 22 | 4 | 3 | 31 | 28 | 33 | 20 | 19 | 25 |
| Amphotericin | 50 | 15 | 9 | 56 | 51 | 48 | 55 | 65 | 64 |
| Ketoconazole | 82 | 39 | 37 | 94 | 103 | 78 | 120 | 122 | 95 |

These data indicate that the tested compound of formula (I) is about twice as effective as amphotericin B in killing the fungi, i.e., in fungicidal activity, and about four times as effective as ketoconazole.

EXAMPLE 10
Serial Dilution Assay

Serial dilution assays of 3,5-dibromo-2,6-dinitrobenzoic acid and nystatin were performed on *Candida albicans*, Trichophyton or Asperigillus. 9 ml ($1 \times 10^4$ cells) of each diluted yeast suspension was added to 1 ml of various serial dilutions of the drug to be tested in 15 ml centrifuge tubes. The final drug concentrations ranged from 0.1 to 0.0001 mg/ml. Two control tubes were also prepared using DDW instead of a drug solution. The tubes were capped and incubated for 24 hours at 30° with shaking at 200 rpm. The fungal growth was assessed by measuring optical density at 600 nm using a nephelometer. Both 3,5-dibromo-2,6-dinitrobenzoic acid and nystatin completely inhibited fungal growth for each *Candida albicans*, trichophyton and asperigillus at a final concentration of 1.5 μg/ml. It is noted, however, that nystatin has a significantly higher toxicity than the compound of the invention tested.

EXAMPLE 11
Toxicity Tests

The acute intravenous toxicity of 3,5-dibromo-2,6-dinitrobenzoic acid in mice is assessed by determining the mean lethal dose ($LD_{50}$) using a well-known method. Mice are fed a standard laboratory diet for 8–10 weeks. Five animals of each sex are administered one intravenous dose of 3,5-dibromo-4,6-dinitrobenzoic acid. The animals are observed for 14 days, and the number of deaths noted. The $LD_{50}$ value is determined to be about 240 mg/kg.

Although the compounds of formula (I) have been synthesized previously, their use as safe, efficacious antifungal agents, suitable for animal, including human, use is heretofore not known.

EXAMPLE 12
Synthesis of chloroanhydride of 3,5-dichloro-2,6-dinitrobenzoic acid

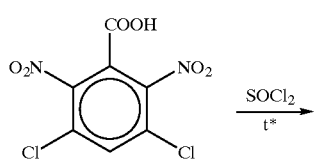

13
-continued

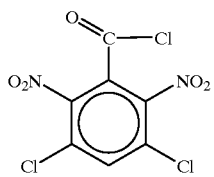

A mixture of 4 g of 3,5-dichloro-2,6-dinitrobenzoic acid, prepared as in Example 2, and 20 ml of thionychloride was boiled for 3 hours. Excess thionylchloride was evaporated under vacuum, leaving a chloroanhydride of 3,5-dichloro-2,6-dinitrobenzoic acid which was used without further purification in the synthesis of the compounds of some of the following examples. The chloroanhydride had the following IR (KBr) absorption peaks: 1778, 1207 (—COCl); 1550 (NO); 733 (C—Cl).

EXAMPLE 13

Synthesis of a 3,5-dichloro-2,6-dinitrobenzoic acid derivative having an amino acid spacer.

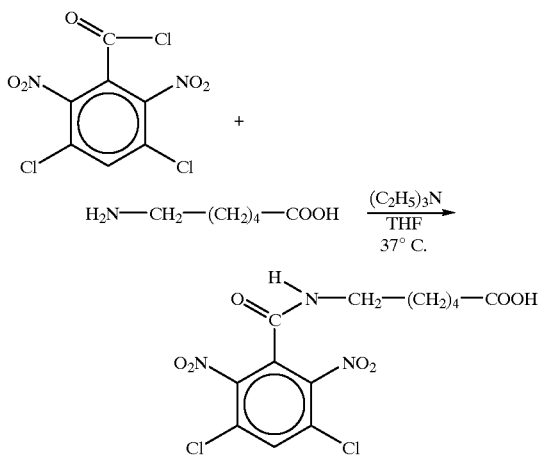

Approximately 1 mM of the chloroanhydride product of Example 12 in 1.2 ml of absolute tetrahydrofuran (THF) was mixed with 144 mg of 6-aminohexanoic acid (1.1 mM) and with 417 µl (303 mg, 3.0 mM) of triethylamine. The mixture was stirred overnight at 37° C. After evaporating the THF under vacuum, the residue was dissolved in a 10% solution of sodium bicarbonate in water. The undissolved material was removed by filtration and the supernatant was precipitated again with 3M HCl (final pH=1.0). The product was recrystallized in 50% methanol, resulting in a 47% yield (188 mg). The product had an uncorrected melting point of 227±1° C. and the following IR (KBr) absorption peaks: 1685 (CO), 1660 (CONH), 1555 (NO). The $R_f^5$ was 0.85. The $R_f^6$ was 0.35.

The product of this example can be considered in two ways. First, it is an intermediate aromatic derivative with a spacer that can accept a ligand at its reactive COOH group. Alternatively, it may itself function as a useful compound within the scope of the present invention, with an N spacer and an alkyl ligand.

EXAMPLE 14

Synthesis of a 3,5-dichloro-2,6-dinitrobenzoic acid derivative having an alcohol spacer.

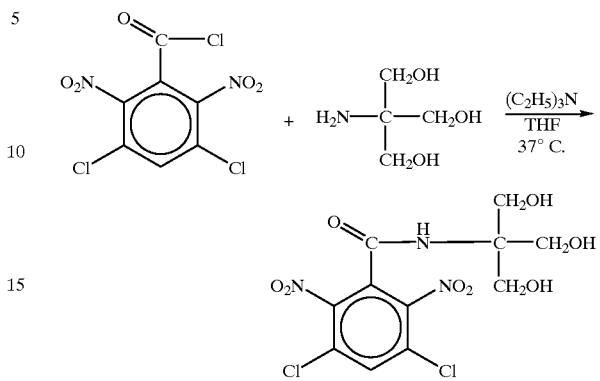

Approximately 10 mM of the chloroanhydride product of Example 12 was dissolved in 10 ml of absolute THF and was mixed with 2.42 g (20 mM) of TRIS {(hydroxymethyl) aminomethane} and with 1.39 ml (1.01 g, 10 mM) of triethylamine. The reaction mixture was stirred overnight (~16 hours) at 37° C. The reaction mixture was then filtered. The crystalline precipitate on the filter was rinsed twice with 1 ml of THF and five times with 5 ml of distilled water to remove excess TRIS. The product was used without further purification. The yield was 78% (3.03 g). The product had an uncorrected melting point of 232±1° C. and the following IR (KBr) absorption peaks: 3300, 1050 (OH), 1660 (CONH), 1555 (NO). The $R_f^6$ was 0.10. The $R_f^7$ was 0.35.

Like the product of Example 13, the product of Example 14 may also be considered in two ways. It is both an aromatic derivative bearing a spacer that can accept a ligand at a hydroxyl group, and an aromatic derivative bearing an spacer (N)- ligand (branched alcohol) combination.

EXAMPLE 15

Synthesis of a 3,5-dichloro-2,6-dinitrobenzoic acid derivative having a diamino polyester spacer.

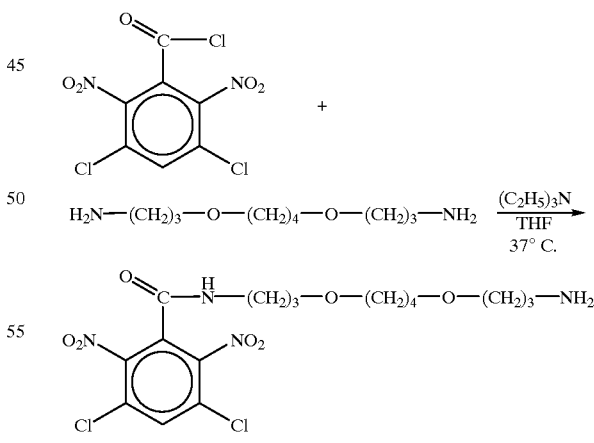

Approximately 10 mM of the chloroanhydride product of Example 12 in 12 ml of absolute tetrahydrofuran (THF) was mixed with 2.12 ml (2.04 g, 10 mM) of 4,9-dioxa-1,12-dodecanediamine and with 1.52 ml (1.01 g, 10 mM) of triethylamine. The mixture was stirred overnight at 37° C. After evaporating the THF under vacuum, the residue was crystallized from 95% ethanol. The yield was 88% (3.78 g).

The product had an uncorrected melting point of 209±1° C. and the following IR (KBr) absorption peaks: 3272, 1111 (NH), 1660 (CONH), 1556 (NO). The $R_f^5$ was 0.85. The $R_f^6$ was 0.35.

EXAMPLE 16

Synthesis of a 3,5-dichloro-2,6-dinitrobenzoic acid derivative having an aminoalkene residue.

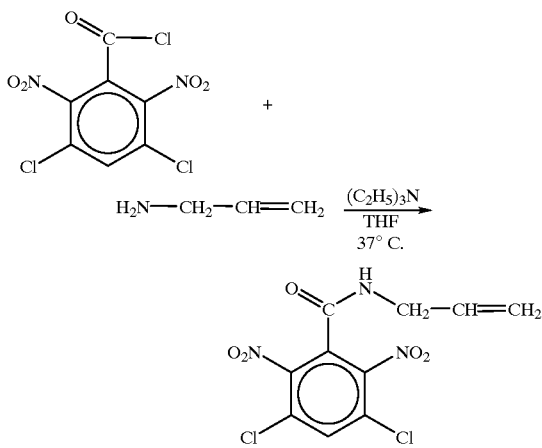

Approximately 5 mM of the chloroanhydride product of Example 12 in 6 ml of absolute THF was mixed with 375 μl (285.5 mg, 5 mM) of allylamine and with 696 μl (505 mg, 5 mM) of triethylamine. The mixture was stirred for two hours at 37° C. The yellow precipitate was filtered, rinsed twice with 1 ml of THF and twice with 1 ml of methanol before being dried under vacuum at room temperature overnight in the dark. The yield was 84% (1.365 g). The product had an uncorrected melting point of 146±1° C. and the following IR (KBr) absorption peaks: 3281, 3080 (NH), 1660 (CONH), 1556 (NO). The $R_f^5$ was 0.20. The $R_f^6$ was 0.80.

The product of Example 16 is itself a functional molecule within the scope of the present invention. Moreover, this molecule provides fungicidal activity at both the allylaminyl ligand and at the aromatic portion. In addition, however, the molecule may also be characterized as merely having a spacer to which a ligand may be attached. Such a second stage addition is demonstrated below in Example 17.

EXAMPLE 17

Synthesis of a 3,5-dichloro-2,6-dinitrobenzoic acid derivative having an aminoalkene spacer and a polymer ligand.

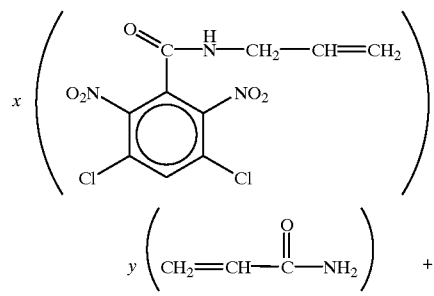

-continued

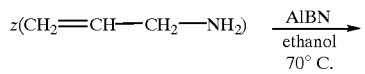

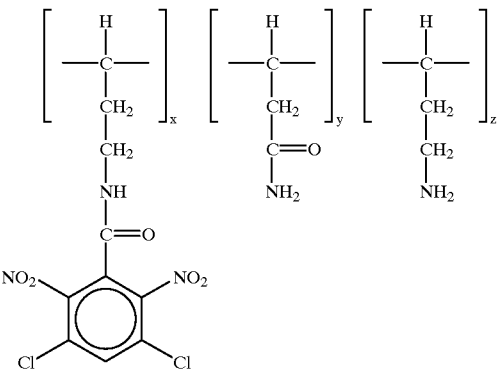

Three monomers (50 mg of the product of Example 16, 850 mg of acrylamide, and 100 mg of allylamine (131 μl)) were stirred overnight at 70° C. with 10 mg of 2,2'-azobisisobutyronitrile (AIBN) in 10 ml of ethanol to form a polymer ligand attached to the substituted benzoic acid via the amine spacer. The resulting suspension was filtered and the filtrate was evaporated under vacuum. The residue was cleaned by preparative thin layer chromatography in a solvent of heptane:methanol:ethylacetate (50:25:25). The yield was 23% (230 mg). The product had an uncorrected melting point of 140±1° C. and the following IR (KBr) absorption peaks: 3281, 600 (NH), 1660 (CONH), 1560 (NO). The $R_f$ in heptane:methanol:ethylacetate (50:25:25) was 0.40. The $R_f^7$ was 0.30.

EXAMPLE 18

Synthesis of a 3,5-dichloro-2,6-dinitrobenzoic acid derivative having a carbohydrate ligand.

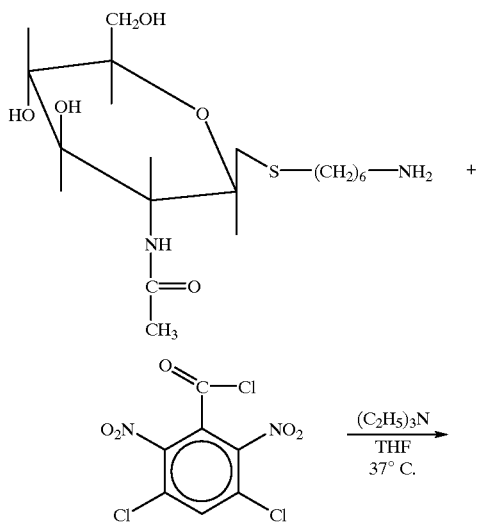

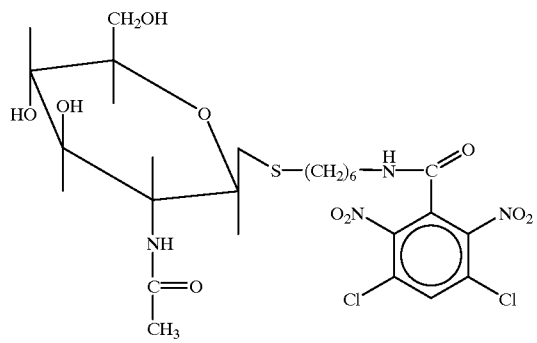

0.1 mM (33.6 mg) of 6-aminohexyl-N-acetyl-β-d-thioglucosaminide was mixed with approximately 0.2 mM of the chloroanhydride product of Example 12 in 1 ml of absolute THF and 28 μl (27.8 mg, 0.2 mM) of triethylamine. The reaction mixture was stirred overnight at 37° C. One ml of 0.1 M HCl was added to the reaction mixture. Some of the added chloride ions formed a volatile chloride salt of triethylamine which was evaporated, along with the THF, under vacuum. The chloroanhydride reactant hydrolyzed to form 3,5-dichloro-2,6-dinitrobenzoic acid which precipitated under the acidic reaction conditions. The precipitated excess of 3,5-dichloro-2,6-dinitrobenzoic acid was removed by centrifugation and the filtrate was lyophilized. Yellow residue was crystallized from ethanol. The yield was 58.6% (35.4 mg). The product had an uncorrected melting point of 230±1° C. and the following IR (KBr) absorption peaks: 3300, 1110 (OH), 2930 (CH), 1660 (CONH), 1555 (NO). The $R_f^5$ was 0.35. The $R_f^7$ was 0.65.

EXAMPLE 19

Synthesis of a 3,5-dichloro-2,6-dinitrobenzoic acid derivative having a carbohydrate ligand.

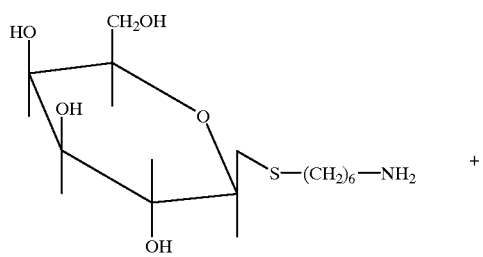

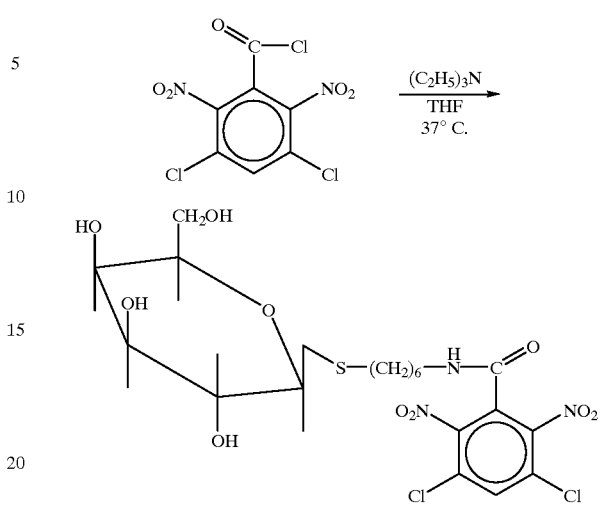

0.1 mM (29.5 mg) of 6-aminohexyl-1-thio-β-d-galactopyranoside was mixed with approximately 0.2 mM of the chloroanhydride product of Example 12 in 1 ml of absolute THF and 28 μl of triethylamine. The mixture was stirred overnight at 37° C. One ml of 0.1 M HCl was added to the reaction mixture. As in the previous example, some of the added chloride ions formed a volatile chloride salt of triethylamine which was evaporated, along with the THF, under vacuum. The chloroanhydride reactant hydrolyzed to form 3,5-dichloro-2,6-dinitrobenzoic acid which precipitated under the acidic reaction conditions. The precipitated excess of 3,5-dichloro-2,6-dinitrobenzoic acid was removed by centrifugation and the filtrate was lyophilized. Yellow residue was crystallized from ethanol. The yield was 64.3% (36.2 mg). The product had an uncorrected melting point of 235±1° C. and the following IR (KBr) absorption peaks: 3275, 1113 (OH), 2924 (CH), 1660 (CONH), 1555 (NO). The $R_f^5$ was 0.30. The $R_f^7$ was 0.60.

EXAMPLE 20

Synthesis of a 3,5-dichloro-2,6-dinitrobenzoic acid derivative having a lipid ligand.

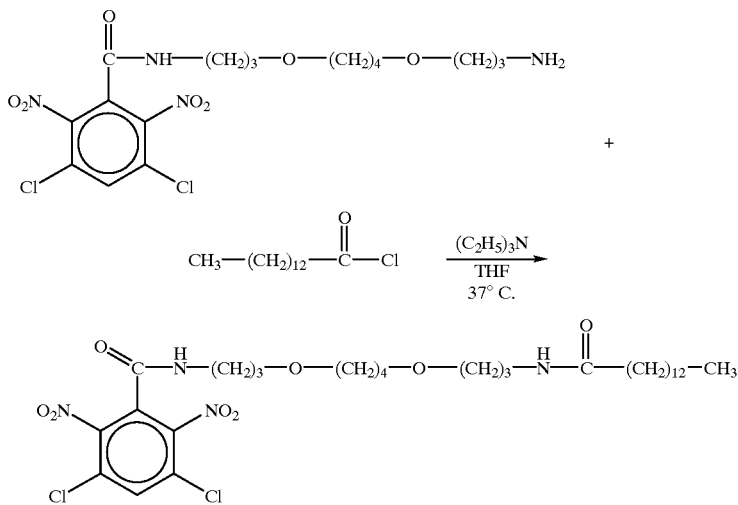

To 5 ml of a solution containing 472 mg (1 mM) of the aminopolyester product of Example 15 in absolute THF, 5 ml of a solution of 247 mg (1 mM) of myristoyl chloride in absolute THF and 278 μl (202 mg, 2 mM) triethylamine was added. The reaction mixture was stirred for two hours at 37° C. After cooling, the yellow crystalline precipitate was filtered, rinsed three times with 1 ml of THF, then dried. The yield was 94% (641 mg). The product had an uncorrected melting point of 176±1° C. and the following IR (KBr) absorption peaks: 2900 (CH), 1660 (CONH), 1555 (NO). The $R_f^5$ was 0.75. The $R_f^6$ was 0.20.

EXAMPLE 21

Synthesis of a 3,5-dichloro-2,6-dinitrobenzoic acid derivative having a steroid ligand.

yellow crystalline precipitate was filtered, rinsed three times with 1 ml THF and dried. The yield was 86% (706 mg). The product had an uncorrected melting point of 196±1° C. and the following IR (KBr) absorption peaks: 3300, 2900 (CH), 1660 (CONH), 1555 (NO). The $R_f^5$ was 0.80. The $R_f^6$ was 0.25.

EXAMPLE 22

Synthesis of a 3,5-dichloro-2,6-dinitrobenzoic acid derivative having a nitrogen-containing positively charged group as a ligand.

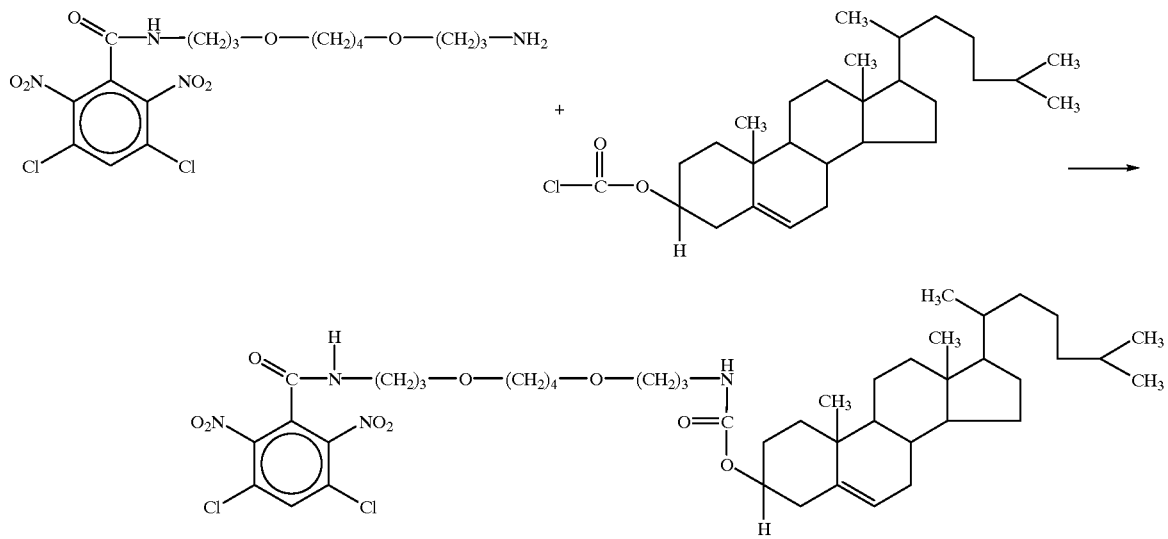

To the solution of 472 mg (1 mM) of the aminopolyester product of Example 15 was added 5 ml of the solution of 449 mg (1 mM) of cholesteryl chloroformate in absolute THF and 278 μl (202 mg, 2 mM) of triethylamine. The reaction mixture was stirred overnight at 37° C. After cooling, the

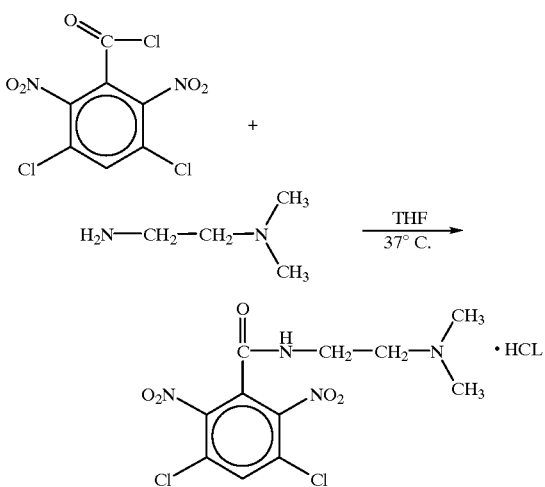

1.0 mM of the chloroanhydride product of Example 12 in 2 ml of absolute THF was mixed with 12.1 μl of N,N-dimethylethylenediamine (96.8 mg, 1.1 mM). The mixture was stirred for three hours at 37° C. After cooling, the THF was evaporated under vacuum. The yellow residue was crystallized from ethanol and was dried. The yield was 89% (317 mg). The product had an uncorrected melting point of 230±1° C. and the following IR (KBr) absorption peaks: 2900, 2700 (CH), 1653 (CONH), 1541 (NO). The $R_f^6$ was 0.20. The $R_f^7$ was 0.45.

EXAMPLE 23

Synthesis of a 3,5-dichloro-2,6-dinitrobenzoic acid derivative having a vitamin as a ligand.

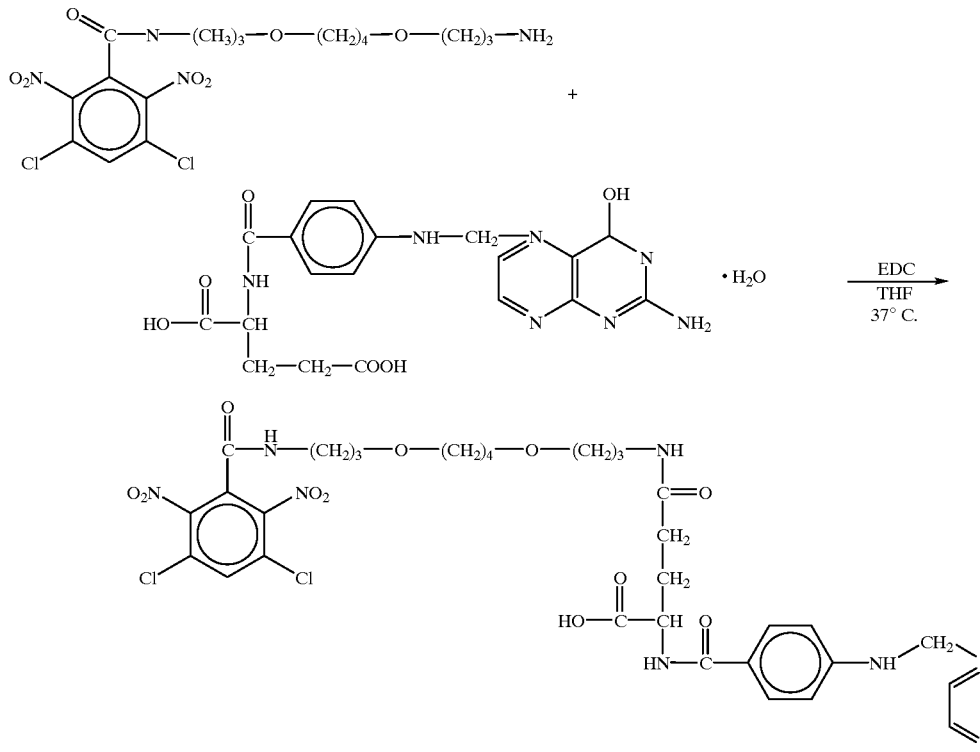

A mixture of 477.4 mg of folic acid dihydrate (1.0 mrM), 269 mg of 3,5-dichloro-2,6-dinitrobenzoic acid (1 mM) and 287.5 mg (1.5 mrM) of 1-ethyl-3-(3-dimethylaminopropyl) carbodiimide (EDC) in 10 ml of absolute THF was stirred at 37° C. for 48 hours. The yellow precipitate was filtered, rinsed twice with hot water, and dried. The yield was 46% (343 mg). The product had an uncorrected melting point of 260±1° C. and the following IR (KBr) absorption peaks: 3350 (NH), 2950 (CH), 1700 (COOH), 1676 (CONH), 1556 (NO). The $R_f^7$ was 0.20. The $R_f^8$ was 0.40.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

I claim:

1. A pharmaceutical composition usefull for treating fungal infections, comprising an effective antifungal amount of a compound of the formula (I):

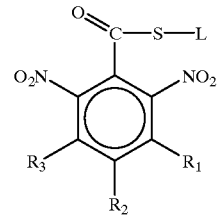

wherein S is a spacer selected from a nitrogen, an oxygen, an alkyl, an alkenyl, an alcohol, an ester, a polyester, an amino acid, a carbohydrate, or a nitrogen-containing positively charged group;

L is a ligand selected from a hydrogen, a hydroxyl residue, an alkyl residue, an alkenyl residue, a benzyl residue, an alcohol residue, an ester residue, a polyester residue, an alkyl acid residue, a carbohydrate, a steroid, a lipid, an organic polymer, a nitrogen-containing positively charged group, or a vitamin;

$R_1$ and $R_3$ are halogen; and $R_2$ is hydrogen or alkyl, provided that L is not hydrogen when S is oxygen and $R_2$ is hydrogen or methyl, and provided that L is not a methyl, ethyl, or benzyl residue when S is oxygen, and addition salts, hydrates, and solvates thereof in combination with a pharmaceutically accepted vehicle.

2. The pharmaceutical composition of claim 1, wherein S or the S-L combination is a 6-aminohexanoic acid residue.

3. The pharmaceutical composition of claim 1, wherein S or the S-L combination is a TRIS {(hydroxylmethyl) aminomethane} residue.

4. The pharmaceutical composition of claim 1, wherein S or the S-L combination is a 4,9-Dioxa-1,12-dodecanediamine residue.

5. The pharmaceutical composition of claim 1, wherein S or the S-L combination is an allylamine residue.

6. The pharmaceutical composition of claim 5, wherein S only is an allylamine residue and L is a acrylamide polymer.

7. The pharmaceutical composition of claim 1, wherein said compound is a 6-aminohexyl-N-acetyl-β-d-thioglucosaminide derivative of 3,5-dichloro-2,6-dinitrobenzoic acid.

8. The pharmaceutical composition of claim 1, wherein said compound is a 6-aminohexyl-1-thio-β-d-galactopyranoside derivative of 3,5-dichloro-2,6-dinitrobenzoic acid.

9. The pharmaceutical composition of claim 1, wherein L is a myristoyl residue.

10. The pharmaceutical composition of claim 1, wherein L is a cholesteryl residue.

11. The pharmaceutical composition of claim 1, wherein L is a N,N-dimethylethylenediamine residue.

12. The pharmaceutical composition of claim 1, wherein L is a folic acid residue.

13. A composition comprising the following formula:

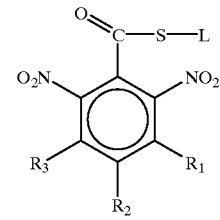

wherein S is a spacer selected from a nitrogen, an oxygen, an alkyl, an alkenyl, an alcohol, an ester, a polyester, an amino acid, a carbohydrate, or a nitrogen-containing positively charged group;

L is a ligand selected from a hydrogen, a hydroxyl residue, an alkyl residue, an alkenyl residue, a benzyl residue, an alcohol residue, an ester residue, a polyester residue, an alkyl acid residue, a carbohydrate, a steroid, a lipid, an organic polymer, a nitrogen-containing positively charged group, or a vitamin;

$R_1$ and $R_3$ are halogen; and $R_2$ is hydrogen or alkyl;

provided that L is not hydrogen, or a methyl, ethyl, or benzyl residue when S is oxygen.

* * * * *